(12) United States Patent
Sramek et al.

(10) Patent No.: US 6,849,051 B2
(45) Date of Patent: Feb. 1, 2005

(54) DEVICES AND METHODS FOR EXTRACTION OF BONE MARROW

(75) Inventors: Roger Sramek, Sausalito, CA (US); Roger S. Smith, Sausalito, CA (US)

(73) Assignee: StemSource LLC, Sausalito, CA (US)

( * ) Notice: Subject to any disclaimer, the term of this patent is extended or adjusted under 35 U.S.C. 154(b) by 0 days.

(21) Appl. No.: 10/212,003

(22) Filed: Aug. 2, 2002

(65) Prior Publication Data

US 2003/0055373 A1 Mar. 20, 2003

Related U.S. Application Data

(60) Provisional application No. 60/310,304, filed on Aug. 3, 2001.

(51) Int. Cl.[7] .............................................. A61B 10/00
(52) U.S. Cl. ....................................................... 600/565
(58) Field of Search ................................ 600/562–572; 604/164.1, 176

(56) References Cited

U.S. PATENT DOCUMENTS

| | | | |
|---|---|---|---|
| 4,393,872 A | * 7/1983 | Reznik et al. | 604/151 |
| 5,012,818 A | * 5/1991 | Joishy | 600/567 |
| 5,462,062 A | * 10/1995 | Rubinstein et al. | 600/567 |
| 5,885,226 A | * 3/1999 | Rubinstein et al. | 600/564 |
| 6,478,751 B1 | * 11/2002 | Krueger et al. | 600/566 |

* cited by examiner

Primary Examiner—Max F. Hindenburg
Assistant Examiner—Pamela Wingood
(74) Attorney, Agent, or Firm—David E. Lovejoy (57) ABSTRACT

This invention provides medical devices and methods for extracting cellular samples from a bone cavity.

32 Claims, 11 Drawing Sheets

DEVICES AND METHODS FOR EXTRACTION OF BONE MARROW

CROSS-REFERENCE TO RELATED APPLICATIONS

This application is a continuation-in-part of provisional patent application U.S. Ser. No. 60/310,304, entitled "Devices and Methods for Extraction of Bone Marrow" by Sramek and Smith, filed Aug. 3, 2001. Applicants claims priority to and benefit of the provisional application, which application is incorporated herein by reference in its entirety for all purposes.

FIELD OF THE INVENTION

The invention relates to devices and methods for collecting samples; more specifically, the invention relates to medical devices and methods for extracting cellular samples from a bone cavity.

BACKGROUND OF THE INVENTION

Bone marrow exists in hollow spaces within bones and acts as a nursery for many of the cellular components of peripheral whole blood. Among the blood cells produced in bone marrow are erythrocytes (red blood cells), platelets (clotting cells) and leukocytes (white blood cells). These blood cells all develop from the so called "stem cells," which are cells in the bone marrow that are capable of both propagating additional stem cells as well as developing into all three types of blood cells.

Stem cells, pluripotential cells and blasts in the bone marrow are very active in cell division to continuously replace blood cells. Without adequate blood cell replacement, patients can develop anemia, clotting disorders and failed immune responses. The extensive cell division activity of the stem cells makes the bone marrow particularly sensitive to therapeutic treatments which are directed at quickly dividing cancer cells, such as chemotherapy and radiation therapy. As a result, it is not unexpected that cancer patients undergoing intensive therapies can sustain life-threatening damage to their bone marrow. Other disease indications may give rise to patients sustaining severe damage to their bone marrow, radiation sickness, aplastic anemia, and cancer metastasis to bone marrow. Bone marrow replacement is often the only available cure for some of these maladies.

Replacement bone marrow can come from the patient (autologus marrow) or from a donor (allogeneic marrow). Bone marrow is typically harvested from large bones near the skin, such as the iliac crest of the hip or the sternum, by pushing a stout needle through the hard outer bone cortex to capture a core sample of bone marrow tissue. A vacuum (i.e., less than atmospheric pressure) is applied to the needle bore to aspirate fluids from the bone including blood and loose marrow cells. Before such a bone marrow harvest can be infused in to a recipient patient, stem cells are typically separated from the connective tissue of the core sample and the mature peripheral blood cells in the aspirated fluid. In order to obtain enough bone marrow to supplement or reconstitute a functional bone marrow in a patient, the puncture and aspiration procedure is generally repeated many times, e.g., 25–50 times in each iliac crest. General anesthesia is commonly used to reduce the emotional stress and pain of the repeated punctures; however, infliction of multiple wounds compound the bone pain, bruising and infection potential of the procedure.

In view of the above, a need exists for a device and methods to obtain bone marrow from a smaller number of bone punctures. Benefits can also be realized from methods that provide a higher ratio of stem cells compared to connective tissue and peripheral blood cells. The present invention provides these and other features that will be apparent upon review of the following.

SUMMARY OF THE INVENTION

The present invention provides devices and methods for extracting material from a cavity, such as a bone cavity. The devices include a housing having a lumen running the length of the housing, a first lumen aperture at a first end of the housing, and a second lumen aperture at a second end of the housing. Within the lumen is placed a plunger body, which is capable of being moved along the length (or a portion of the length) of the lumen. One or more filaments are coupled to one end of the plunger body, and positioned proximal to the first end of the housing. At another position along the plunger body, a handle or other mechanism for moving the plunger body is attached, such that the handle extends beyond the housing. In addition, an aspiration tube is cojoined to a portion of the housing, wherein the aspiration tube comprises a first aspiration aperture typically positioned proximal to the first lumen aperture.

Optionally, the housing of the device further includes a piercing mechanism, such as, e.g., a cutting and/or puncturing tool, positioned proximal to the first lumen aperture. In a preferred embodiment, the first lumen aperture and the first aspiration aperture are adjacently positioned, such that the housing and aspiration tube together provide the piercing mechanism for insertion of the apertures into the bone cavity.

The housing can further include a stop at the second end of the housing (e.g., typically distal from the insertion end). The stop can be used, for example, to meter extension of the filament into the bone cavity (e.g., by monitoring the distance between the stop and the handle). In some embodiments of the present invention, the plunger body includes a portion having a screw thread, which matches up with inner screw threads within the lumen interior. In this embodiment, as the handle of the device is turned, the plunger body is moved relative to the housing lumen, and the attached filament components are extended from the lumen aperture in a meterable manner.

The filament portion of the devices of the present invention can include a variety of embodiments, including, but not limited to, a single filament, a filament having one or more extensions, or multiple filaments. In some embodiments, for example, the filament is a rigid piece of plastic or metal (e.g., stainless steel or titanium) having one or more looped extensions. Shape memory wire is particularly useful for use in the filaments of the present invention.

Optionally, the filament portion of the device further includes a mechanism for associating a portion of the filament with a surface within the bone cavity (for example, a notch or point that can engage or be embedded in the far wall of the bone cavity). Using this filament embodiment, the rotation of the filament and disruption of the local cellular matrix can be performed more efficiently and/or accurately.

In many embodiments, the filament includes a cutting edge which assists in the matrix disruption. The cutting edge can run only a portion of the filament length, or it can be include along the entire length of the filament.

Rotation of the filament within the bone cavity can be accomplished by a number of mechanisms. In some embodiments, the filament is rotated by turning the handle portion of the device. Optionally, the handle is an ergonomically-shaped member positioned perpendicular to the length of the plunger body. Alternatively, the handle comprises a knob or cog mechanism.

The cavity contents disrupted by the filament are retrieved via the aspiration tube portion of the device. Typically, the first aperture of the aspiration tube is positioned proximal to the first lumen aperture (e.g., central to the disrupted area). A vacuum or partial vacuum is applied to a distal portion of the aspiration tube by, for example, a flexible bulb, a syringe, a vacuum pump, and the like. Optionally, a collection device, such as a removable liquid trap, is coupled to the vacuum mechanism for collection of the retrieved material.

In some embodiments of the present invention, the housing is a multi-lumen structure, thereby providing a body structure encompassing both the housing lumen and the aspiration tube. Optionally, the device further includes a sleeve or trocar surrounding the housing and aspiration tube. Such a sleeve can be a strong and sharp cylinder specialized for piercing the solid outer bone cortex.

The present invention also provides devices and methods for delivery of a composition, such as a drug, cell, chemical, or combination thereof, as well as devices and methods for deployment of one or more diagnostic devices inside a cavity, such as a bone cavity.

Definitions

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a surface" includes a combination of two or more surfaces; reference to "bacteria" includes mixtures of bacteria, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

As used herein, the terms "bone cavity" and "bone marrow cavity" refer to the non-cortex interior of bones containing marrow cells (including, but not limited to, hemopoietic stem cells, megakaryocytes, and white cell precursors).

The term "bone cortex" as used herein refers to the outer solid mineralized portion of a bone.

The term "stylus" as used herein refers to a solid insert, typically composed of metal, and used to temporarily fill a lumen or tube in the devices of the invention.

As used herein, the term "trocar" refers to a cylindrical sleeve or collar-like implement which optionally can comprise a piercing tool and into which the housing and/or aspiration tube can be inserted.

As used herein, the term "piercing" also includes, but is not limited to, cutting, slicing, drilling, and puncturing.

The term "slideably" as used herein refers to either a straight linear direction of movement or a spiral or corkscrew-type movement.

BRIEF DESCRIPTION OF THE DRAWINGS

FIG. 1 panels A through E depict one embodiment of the devices of the present invention having a looped filament. Panel A provides a side elevational view of the device; panels B and C provide cross-sectional views of the plunger and housing/aspiration components, respectively; panel D depicts the device with the filament withdrawn, and panel E depicts the device with the filament extended into a bone cavity.

FIG. 4 (FIGS. 4A–4L) depicts various cross-sectional shapes that can be employed in the filaments of the present invention.

FIG. 5 (FIGS. 5A–5C) provides external depictions of the device embodiment provided in FIG. 3.

FIG. 6 (FIGS. 6A–6B) provides a close-up illustration of one embodiment of the filament and optional L-bend.

DETAILED DESCRIPTION

The present invention provides devices and methods for extracting material from a bone cavity. The bone cavity can be any of a number of such cavities, including, but not limited to, cavities in the iliac crest (hip), jaw bone, sternum, tibia, and the like. Material of interest contained within the bone cavity includes, but is not limited to, mesenchymal cells, and undifferentiated pluripotential cells (e.g., stem cells and blasts) that can divide and mature into peripheral blood cells (such as red blood cells, platelets and white blood cells) or other non-blood related cells (neuronal cells, hepatic cells, etc.). In addition to bone marrow, the bone marrow cavities can contain, e.g., a fine bone network of trabecula, a matrix of supporting connective tissue cells (such as fibroblasts), fat cells, and blood cells at various stages of development. It is desirable to harvest bone cavity contents such as stem cells and blasts for use, for example, in reconstitution of bone marrow in a patient.

Acquisition of bone marrow for transplantation or other purposes is typically performed via the repeated insertion of a needle into the bone cavity containing the marrow, thereby collecting multiple "core samples" of tissue from which the relevant cells can be isolated. Exemplary devices for performing the procedure are described in, for example, U.S. Pat. Nos. 5,429,138 and 5,526,821 to Jamshidi "Biopsy needle with sample retaining means", U.S. Pat. No. 5,807, 275 to Jamshidi "Biopsy needle", and references cited therein. Typically, the core sampling procedure (similar to punch biopsy) must be repeated between 25–50 times to obtain enough extraction material (e.g., approximately 1000–1500 milliliters) having the desired marrow volume and/or stem cell count.

The devices and methods of the invention can provide adequate bone marrow extraction (e.g., bone marrow harvests rich in stem cells) for use, e.g., in a bone marrow replacement procedure, in a relatively small volume of aspirate from a smaller number of bone piercings as compared to the prior art. Whereas bone marrow aspiration devices in the prior art harvest a core of tissue directly in line with the entry puncture, and what cells can be aspirated along with a stream of blood, the devices of the invention are designed to release and capture bone marrow cells some distance from the puncture site. The devices of the invention provide, e.g., filaments that can extend laterally from the axis of the puncture to disrupt any trabecula and connective tissue matrices present in the bone cavity, allowing improved release and aspiration of resident stem cells.

Devices for Extraction

Figure 1A:
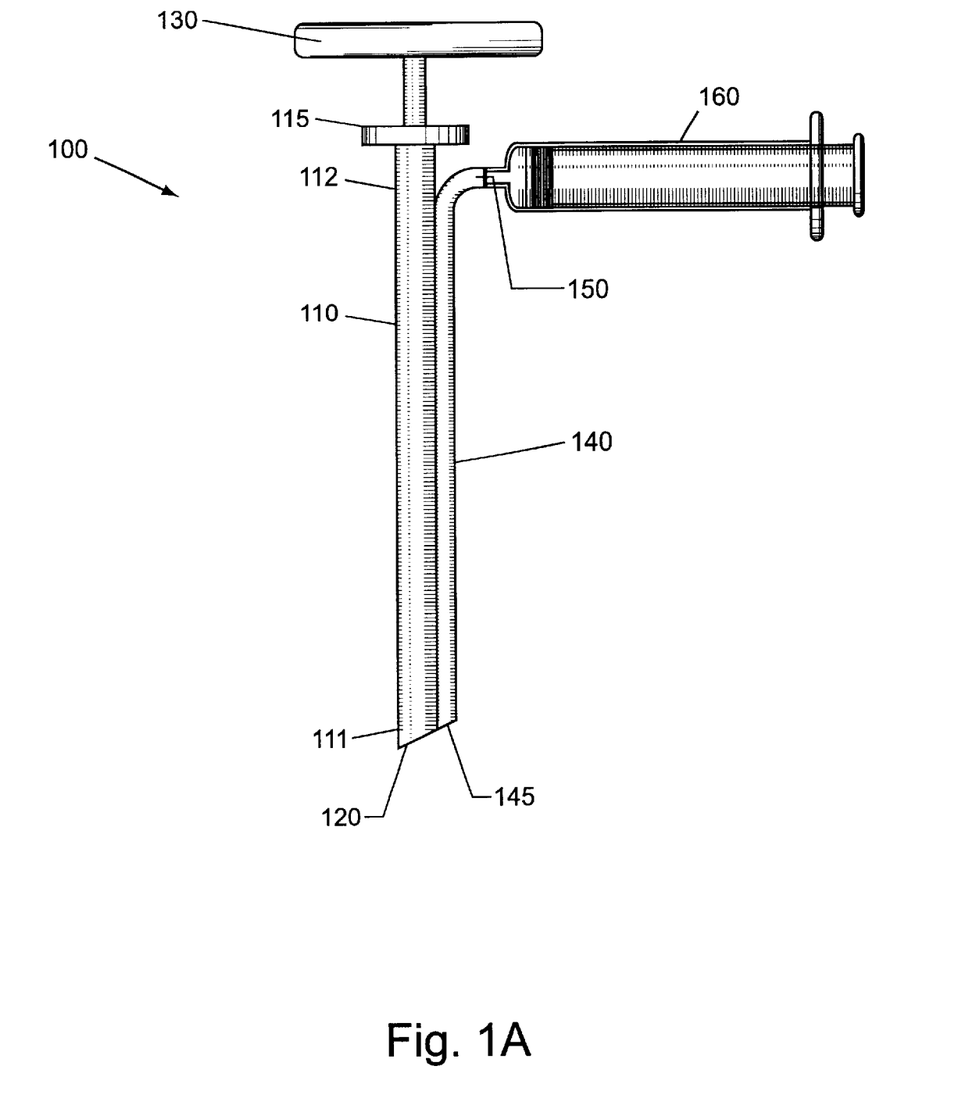
Figure 1B:
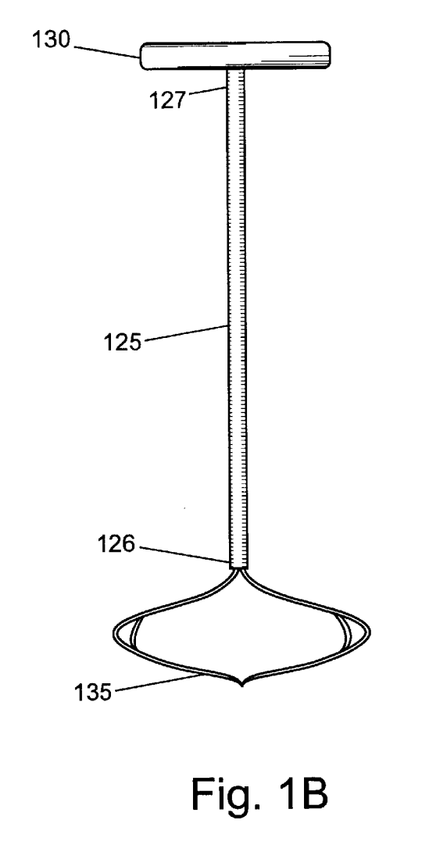
Figure 1C:
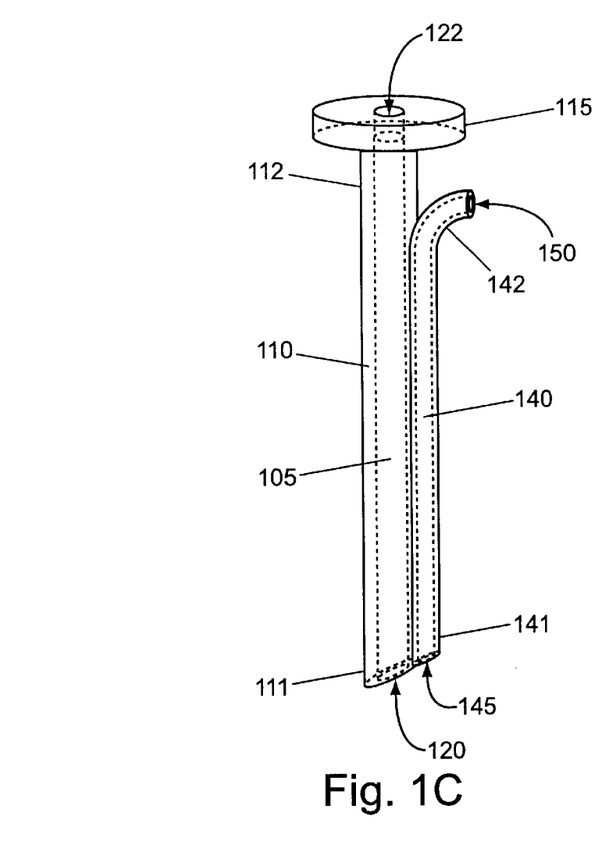
Figure 1D:
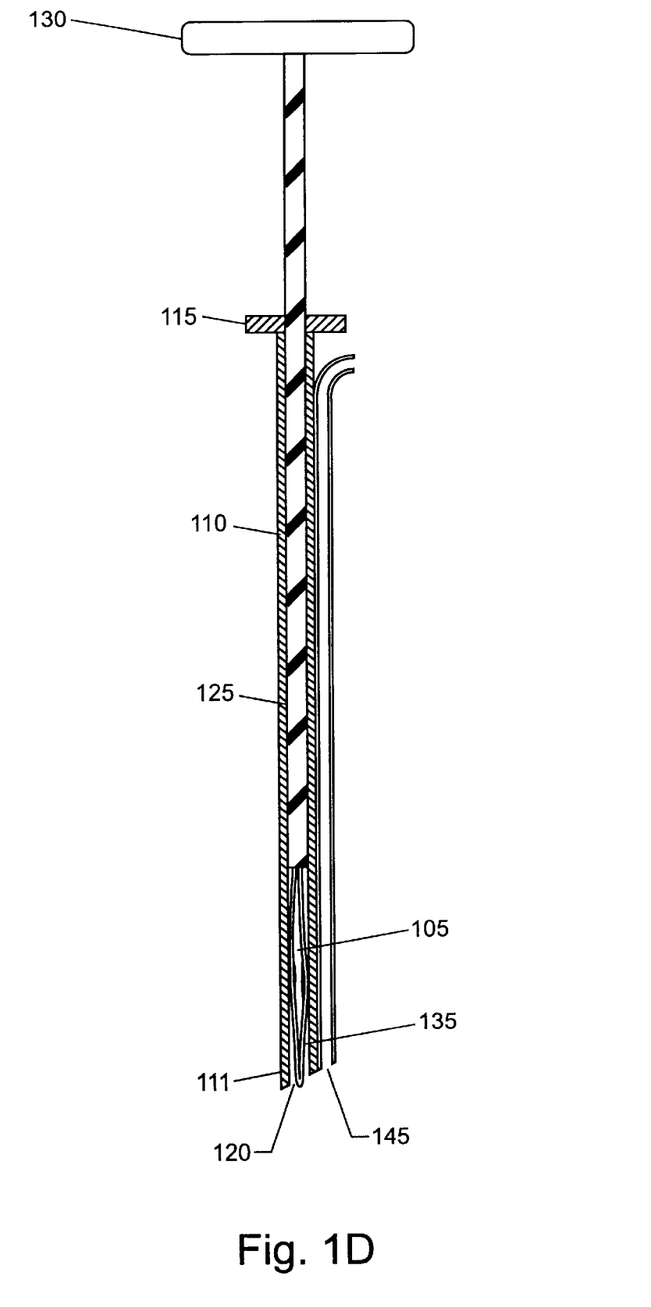
Figure 1E:
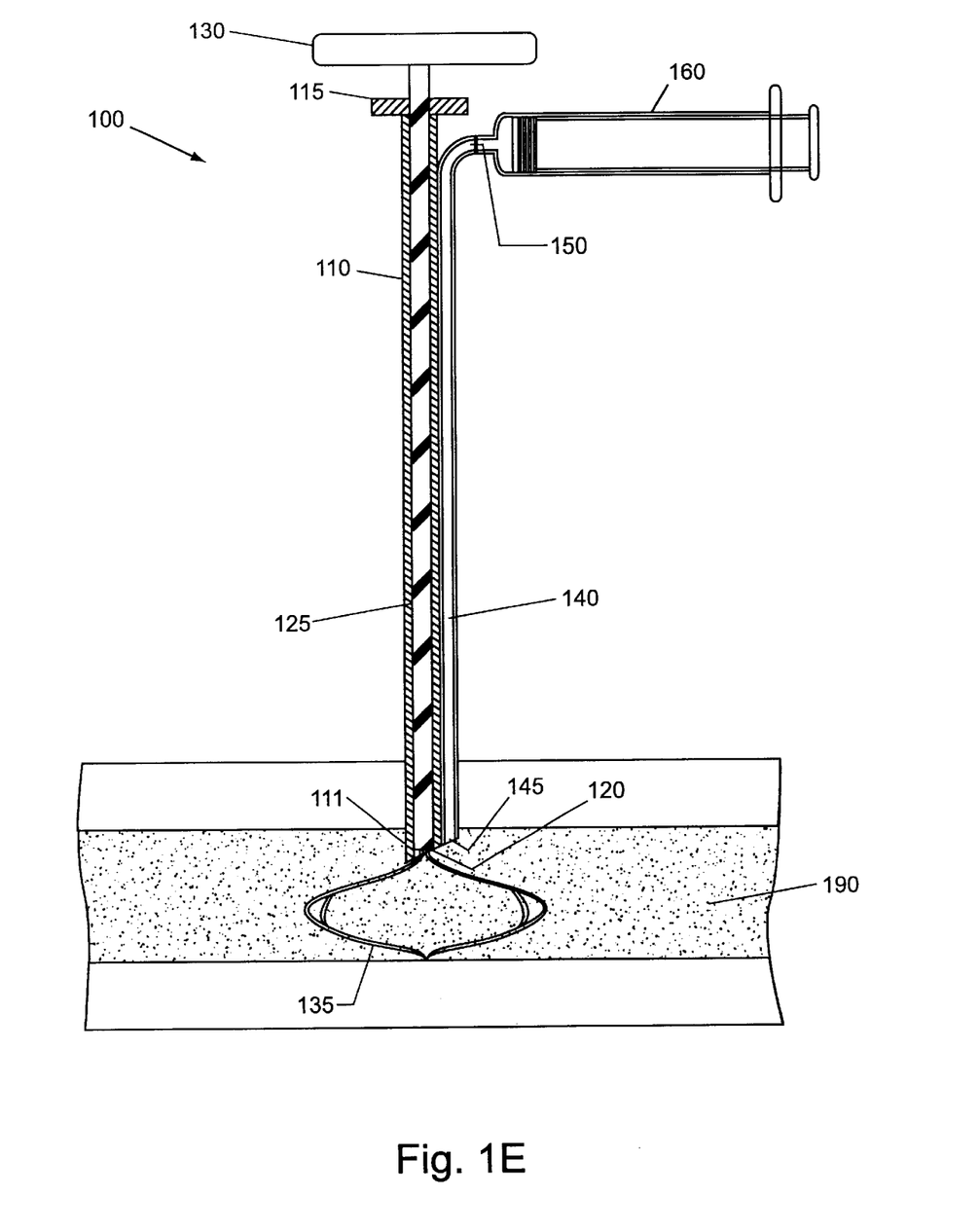

The devices of the present invention include a housing having a lumen running the length of the housing, a plunger body slideably positioned within the housing lumen, and an aspiration tube. One embodiment of the devices of the present invention is shown in FIGS. 1A through E. FIG. 1A provides an exemplary device of the present invention. Two elements of the unassembled device, the plunger portion and the body portion are depicted in FIGS. 1B and 1C, respectively, while FIGS. 1D and 1E portray the assembled device components in the "withdrawn" and "extended" positions.

The components of the devices of the present invention (e.g., the housing, plunger and aspiration tube) can be manufactured from any of a number of appropriate materials known to one of skill in the art and/or typically used (or approved for use) in the medical arts. Exemplary materials include, but are not limited to, various plastics, ceramics, glasses, rubber, metals, and composites (e.g., fiberglass, carbon fiber composites, resins, and the like). For example, the housing can be fabricated from surgical stainless steel to provide a strong inert body to, e.g., receive the working forces of extraction procedures and to present a sharp cutting edge at the proximal end. Preferably, the devices of the present invention are manufactured from materials able to withstand sterilization procedures, e.g., between procedures.

In this embodiment, device 100 includes housing 110 having first housing end 111 (at the end of the device to be positioned proximal to the bone cavity) and second housing end 112 (at the distal end of the device). Housing 110 encompasses lumen 105, which runs at least a portion of the length of housing 110; first lumen aperture 120 at the first end of housing 110; and second lumen aperture 122. In some embodiments (as depicted in, for example, FIG. 1C), second lumen aperture 122 is positioned at second housing end 112 such that lumen 105 runs the length of housing 110. In alternate embodiments, second lumen aperture 122 is positioned between first housing end 111 and second housing end 112. In the embodiment portrayed in FIG. 1, plunger body 125 runs the length of housing 110 and extends beyond optional stop 115 positioned at the second housing end 112, to plunger handle 130.

In other embodiments (not shown) the housing can house both the lumen and aspiration tube in a multi-lumen structure, thus providing a structure with a circular cross section conducive to rotation of the device after insertion into a bone. A sleeve or trocar can optionally be provided to surround the housing and aspiration tube. Such a sleeve can be used, e.g., as a structure to orient a piercing mechanism on the first aperture and/or first opening during insertion, and/or to provide a rotatable cylindrical external shape to the device.

Filament 135 is attached at first end 126 of plunger 125. Filament 135 comprises any of a number of structures that, in the withdrawn position (FIG. 1D), are positioned within housing 110. In the extended position (FIG. 1E), the filament expands into a designed form, or "memory structure," extending from first lumen aperture 120. Optionally, filament 135 comprises stainless steel, surgical stainless steel, nickel-titanium, titanium, and the like.

In the depicted embodiment, filament 135 comprises two looped wires attached to one another at points proximal and distal to aperture 120, as shown in FIG. 1B. Such an arrangement can, e.g., enhance the cutting and scouring ability of the filament while strengthening the operational geometry. Optionally, the filament further includes an optional stabilizing wire (see element 828 in FIG. 8) or an optional bauble (see element 639 in FIG. 6), to enhance the filament action by minimizing collapse of the filament after extension from the housing aperture.

Optionally, the filament structure or stabilizing wire includes a notched or pointed region for embedding the filament (temporarily) in the far wall of the bone cavity, thereby enhancing the lateral movement of the filament through the material within the bone cavity. By pivotably-engaging the end of the extended filament a distance from the aperture, excess filament can be extended into the cavity to sweep a wider volume as the filament is rotated. The wider sweeping filament can reach laterally into cavities in the bone marrow to disrupt more tissue for harvest of cells.

Figure 2:
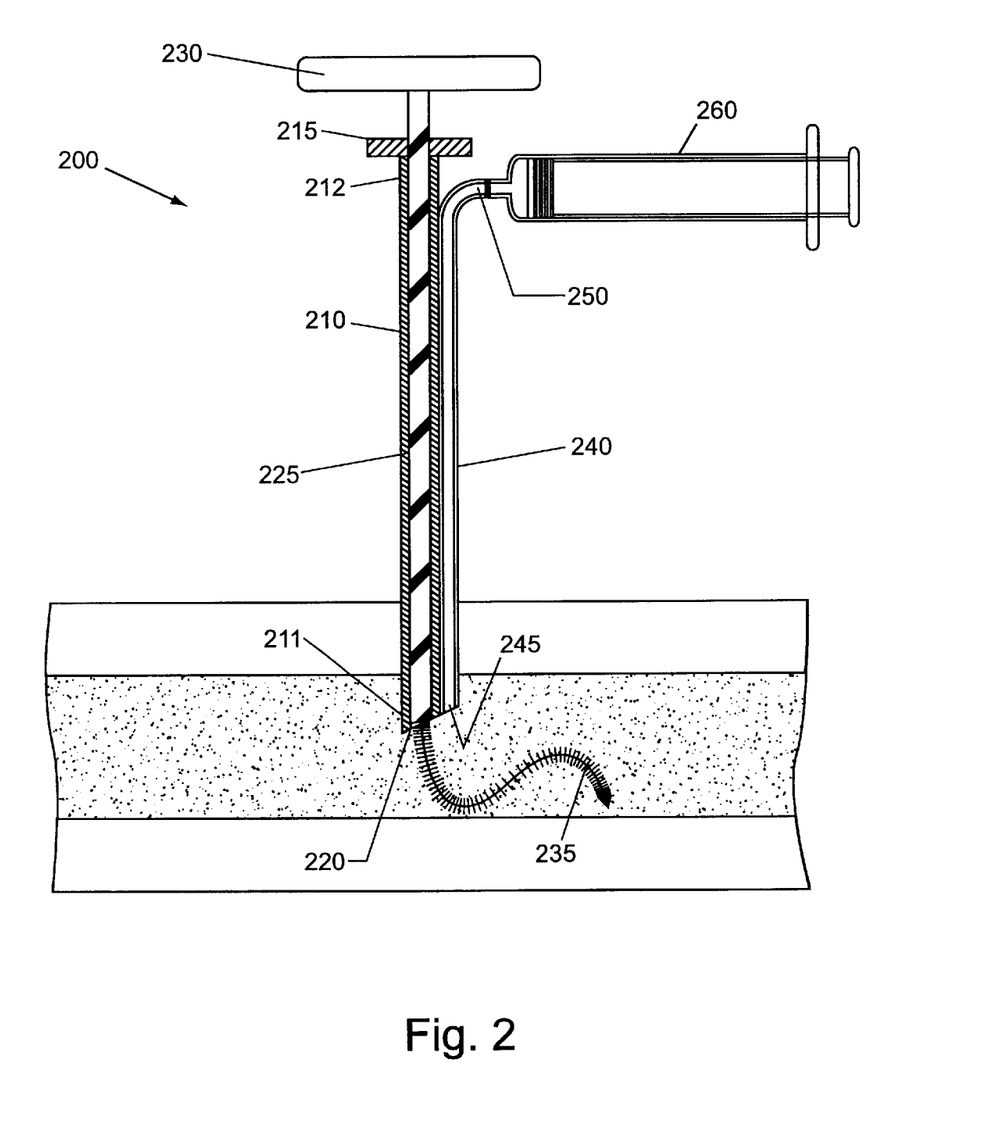
FIG. 2 depicts another embodiment of the devices of the present invention employing a non-looped shape memory filament and a syringe as an aspiration mechanism.

Filament 135 can include a single structure (such as depicted in FIG. 2), a branched or looped structure (see, e.g., FIG. 1B), or a plurality of structures. In one preferred embodiment, the filament comprises a rigid piece of metal, plastic, or the like having multiple cross-members. In another preferred embodiment, the filament comprises a bristled, or brush-like, structure. In still another preferred embodiment, the rigid piece comprises a shape memory wire. However, any of a variety of filament structures can be employed in the present invention. For example, one or more portions of the filament can have a cross-sectional shape as depicted in FIG. 4.

Optionally, filament 135 has a beveled or sharpened edge capable of breaking, scooping, or cutting through the material in the bone cavity. Marrow tissue in many bones, such as long bones of the arms and legs, can be soft and compliant. However, the marrow cavities of some bones, such as the plate-like bones, can include substantial amounts of structural material, such as collagen fibers, connective tissue matrix, and fine bone plates (trabecula). The presence of a cutting edge on the filament can allow the device of the invention to penetrate the structural materials to disrupt a larger volume of bone marrow tissue, thereby releasing more stem cells for harvest.

Device 100 further includes aspiration tube 140 positioned adjacent to (and/or cojoined with) housing 110. Aspiration tube 140 includes a first aspiration tube opening 145 positioned proximal to lumen aperture 120, and a second aspiration tube opening 150. Optionally, second aspiration tube opening 150 is positioned at the distal end of aspiration tube 140. When in use, second opening 150 is connected to mechanism 160 for applying a vacuum (or partial vacuum), such as a vacuum pump or a syringe. A collection device, such as, e.g., a conventional liquid trap, can optionally be located between the aspiration tube and the vacuum mechanism, to harvest aspirate and prevent it from entering the vacuum source. As indicated for the other elements of the extraction device, aspiration tube 140 can comprise any of a number of medically acceptable materials, including, but not limited to metal, plastic, composites, or combinations thereof. Preferably, the interior surface of the aspiration tube includes materials that will not chemically or biologically interact in an undesired manner with the material being extracted from the cavity. Optionally, aspiration tube 140, collection device, and/or mechanism 160, can be treated or contain heparin, hirudin, citrate, or another anticoagulant to prevent occlusion of the aspiration tube and to provide a fluid aspirate for easier processing.

In the depicted embodiment, lumen aperture 120 is positioned at first housing end 111, adjacent to first aspiration tube opening 145 and proximal to the point of entry into bone cavity 190. Entry into the cavity can be accomplished by positioning of a piercing mechanism, e.g., cutting, puncturing, slicing and/or drilling tool, at the proximal end of the device, and driving the tool through the hard external bone cortex material. In some embodiments, aperture 120 is designed to be inserted into the bone cavity, and as such includes the piercing mechanism. For example, the piercing mechanism can be a sharp-edged angular puncturing tool provided at the proximal ends of the housing and aspiration tube. The puncturing portion of the device is preferably placed on the patient's body at a position at which the bone is in close proximity to the skin. The proximal end of the device is then driven through the bone cortex on the surface by, e.g., applying force to a sturdy handle such as plunger handle 130. Alternatively, the piercing mechanism can be incorporated into housing first end 111, or provided by alignment of the first end of the housing with the first end of the aspiration tube (e.g., a cutting means formed by the contiguous housing/aspiration tube surface). Optionally, first opening 145 and lumen aperture 120 function together in providing access to the contents of the bone cavity.

When in use, plunger body 125 is slideably positioned within lumen 105 of housing 110. In the "withdrawn" position (FIG. 1D), filament 135 is contained within lumen 105 during entry of lumen aperture 120 into the bone cavity. Movement of plunger body 125 along lumen 105 in the direction of first housing end 111 advances filament 135 such that it extends from lumen aperture 120. Movement of the plunger body is typically achieved by exerting force upon plunger handle 130. In the embodiment depicted in FIG. 1, optional stop 115 is positioned proximal to second lumen aperture 122, thereby limiting the movement of handle 130 and extension of filament 135 into bone cavity 190.

In some embodiments, plunger body 125 and housing lumen 105 include screw threaded portions. For example, a screw threaded plunger body can be inserted into a lumen having inner screw threads. Turning of the plunger handle controllably extends the filament attached to the proximal end of the plunger into the bone cavity, thereby providing a mechanism for metering the extended state. Alternatively, the housing can be fitted with a rack and pinion, or tooth and pawl ratcheting mechanism, to incrementally meter the plunger movement, as can be appreciated by those skilled in the art.

Optionally, a solid stylus can be placed into the housing lumen and/or the aspiration tube to prevent occlusion of the lumen(s) during the bone penetration. The stylus is then removed prior to extraction of the bone marrow. For example, after penetration of the proximal end of the device into the bone cavity, the stylus can be removed, and a plunger with a filament can be passed through the lumen so that the filament extends into the marrow cavity.

The device of the present invention can include structures ergonomically designed to facilitate the mechanical forces and movements required to insert the devices of the present invention through the cortex of bone to enter the marrow space. The devices can include, e.g., an ergonomically shaped handle (or knob) to receive the force of a surgeon to puncture the bone cortex. Such a handle can be mounted, e.g., to housing, aspirator tube, plunger, sleeve, trocar, or any element of the devise associated with the piercing mechanism, to direct appropriate rotational or vector forces to the piercing mechanism.

The plunger handle 130 can, for example, optionally be used to assist in the insertion of a portion of the device into the bone cavity. In these embodiments, housing 110 preferably provides a locking mechanism (not shown) to immobilize plunger handle 130 in the withdrawn position during insertion of the device. As the forces involved in bone cortex penetration can be significant, the plunger body and handle can be fabricated with the strength to receive, e.g., 70 kg/cm$^2$ of force or repeated blows from a surgical hammer.

Typically, the housing of the devices of the present invention range in length, e.g., from about 2 cm to about 30 cm, and typically have an outer diameter ranging in size from about 2 mm to about 10 mm, or more typically from about 2 mm to about 7 mm. The extraction devices are capable of extracting between about 0.5 mL to about 500 mL of aspirate material from a single piercing of a bone cavity (more typically about 2 mL to about 25 mL, about 25 mL to about 50 mL, or about 26 mL or about 50 mL to about 500 mL).

Another embodiment of the devices of the present invention is shown in FIG. 2. Device 200 includes housing 210, with lumen aperture 220 at first housing end 211 and optional stop 215 positioned at second housing end 212. Housing 210 encompasses (via a corresponding housing lumen) plunger body 225, which runs the length of housing 210 and extends beyond optional stop 215 at the second housing end to plunger handle 230. Filament 235 is attached at the proximal end of plunger 225. In the depicted embodiment, filament 235 comprises a bristled shape memory wire (e.g., a filament that retains memory of the desired shape, and returns to that shape upon release from containment, for example, within a housing). The device depicted in FIG. 2 further comprises syringe 260, attached to second aspiration tube opening 250 of aspiration tube 240. Alternatively, a vacuum pump or vacuum-containing container (e.g., a vacuum jar) can be used in place of syringe 260.

A further embodiment of the devices of the present invention is depicted in FIG. 3. In this embodiment, movement of both the filament as well as the proximal end of the housing are employed to disrupt the cellular framework within the bone cavity prior to aspiration. This embodiment of the device (FIG. 3A) is depicted prior to insertion of the device into the bone cavity (FIG. 3B), after insertion (FIG. 3C), and after extension of the filament (FIG. 3D).

Figure 3A:
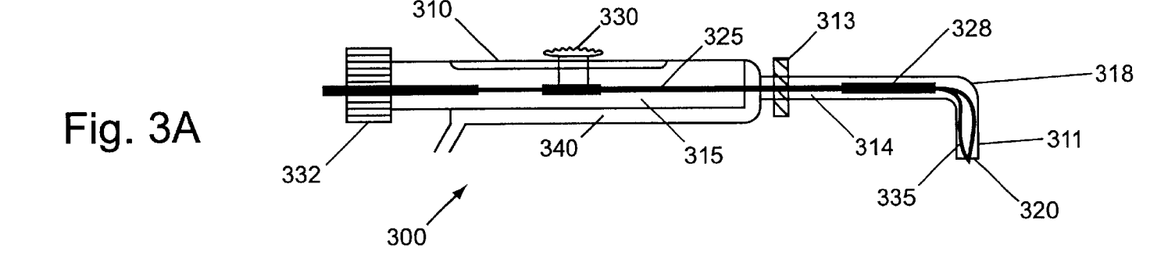
FIG. 3 depicts a further embodiment of the devices of the present invention having an L-bend proximal terminus for added matrix disruption.
Figure 3B:
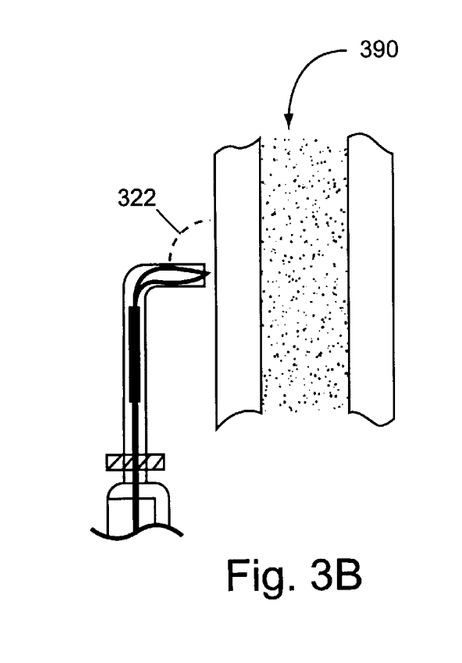
Figure 3C:
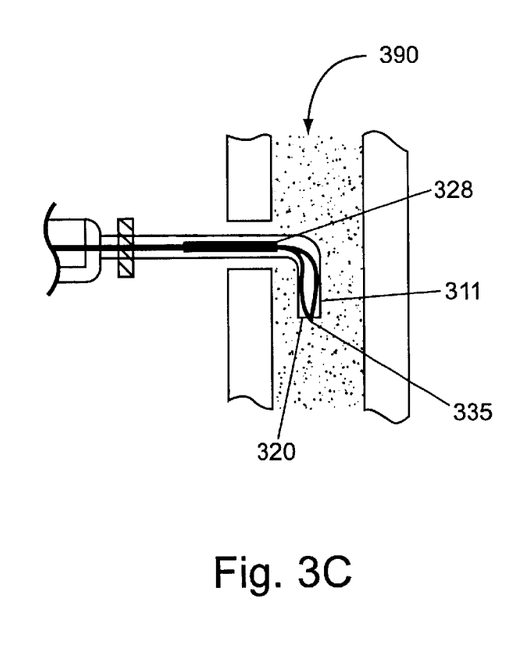
Figure 3D:
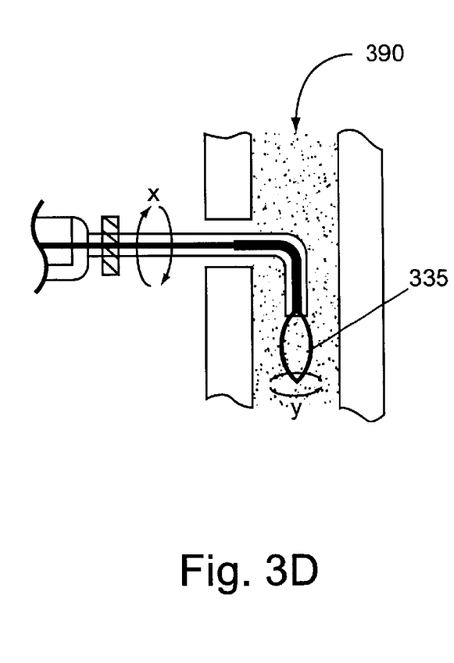
Figure 4A:
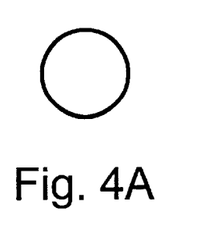
Figure 4B:
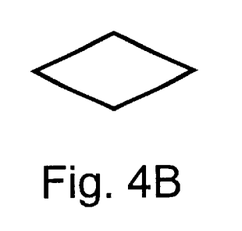
Figure 4C:
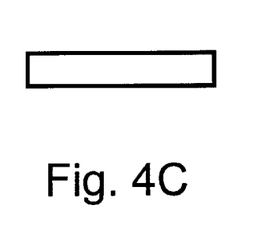
Figure 4D:
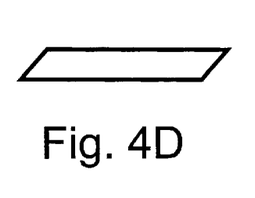
Figure 4E:
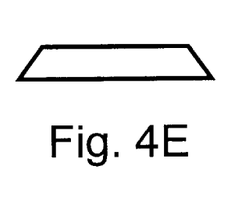
Figure 4F:
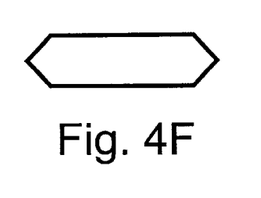
Figure 4G:
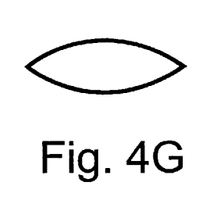
Figure 4H:
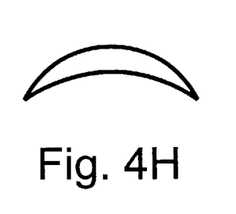
Figure 4I:
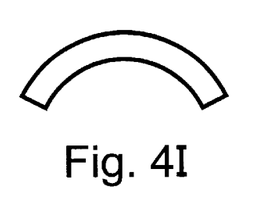
Figure 4J:
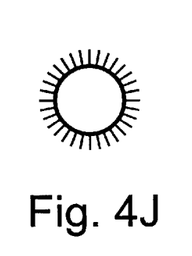
Figure 4K:
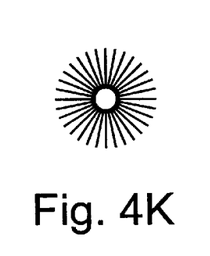
Figure 4L:
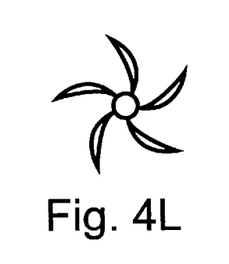

Device 300 includes housing 310, having first portion 315 and second portion 314 connected by swivel joint 313. Second housing portion 314 further includes L-bend 318 and aperture 320 at first, or proximal housing end 311 to be inserted into bone cavity 390 (shown in panels B–D). The length of the housing between the L-bend 318 and aperture 320 is preferably no greater than the inner diameter of bone cavity 390. In one embodiment, this portion of the housing optionally ranges from about 0.25 inches to about 0.375 inches. Swivel joint 313 is positioned between proximal housing end 311 and distal end 312 and can be used to rotate L-bend 318 within bone cavity 390 (see arrow X in FIG. 3D) while maintaining the position of (e.g., not rotating) housing end 312. Housing end 311 optionally has a piercing mechanism (not shown) with a wider diameter than L-bend 318 to facilitate passage of the L-bend through the resulting bone cortex perforation.

Housing 310 encompasses most of plunger shaft 325, which runs the length of housing 310 and is attached to slide (e.g. plunger handle) 330. In the depicted embodiment, slide 330 is attached to plunger shaft 325 in a middle portion of the plunger shaft; however, slide 330 can be positioned at alternate positions along plunger 325. For example, the length of the plunger body can optionally be less than the length of the housing, and the plunger handle or slide can be positioned at or near a terminus of the plunger body.

Plunger shaft 325 further includes plunger portion 328, typically positioned proximal to filament 335. Plunger portion 328 is preferably manufactured from a flexible material, so that portion 328 can be maneuvered through L-bend 318 during extension (and return) of filament 335.

During use, lumen aperture 320 is inserted into bone cavity 390 (FIG. 3B) with concomitant rotation of housing 310 through angle 322, such that first housing end 311 and aperture 320 extend into bone cavity 390 up to and including L-bend 318 (FIG. 3C). Once inserted, filament 335 can be extended from aperture 320, and can optionally expand into the designed memory shape. Either (or both) first housing end 311 or filament 335 can be rotated (e.g., see arrows X and Y respectively in FIG. 3D), either manually or via optional power shaft coupler 332 (which is configured to be coupled to a dental handpiece or other motorized device, not shown), thereby further disrupting the cellular framework within bone cavity 390.

The cavity contents are withdrawn via aspiration tube 340 positioned adjacent to housing 310. In the depicted embodiment, the lumen within first housing end 311 (e.g., the portion proximal to the point of entry into the bone cavity) functions as both the housing lumen containing filament 335 as well as a conduit leading to aspiration tube 340. Alternatively, first housing end 311 can contain multiple lumen, to provide separate filament access and aspiration conduit.

FIG. 4 depicts various cross-sectional shapes which can be employed in the filaments of the present invention. For example, the cross-section of the filament can have a round or circular shape (panel A); a diamond shape (panel B); a rectangular or trapezoidal shape (panels C, D and E), a hexagonal shape (panel F), a crescent shape (panel H), or an arched shape (panel I). Furthermore, the filament can include various shaped bristles or cross-members (panels J, K and L).

Figure 5A:
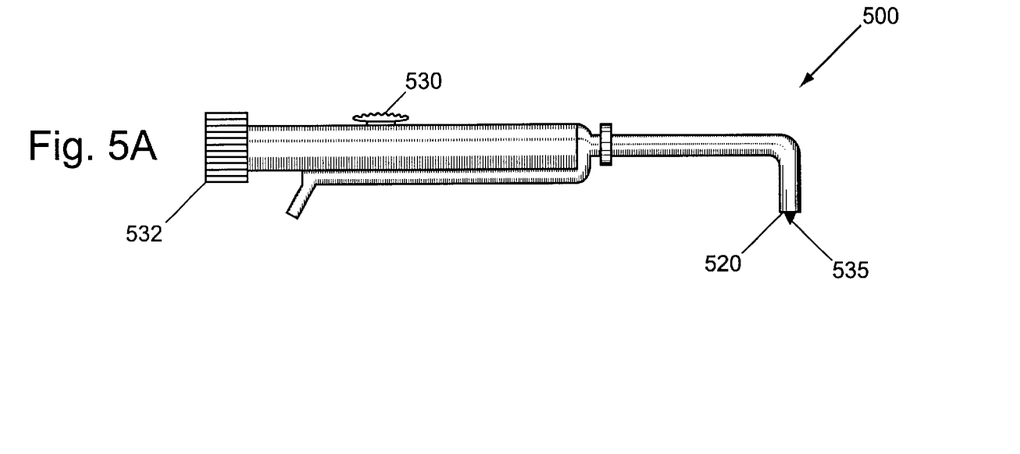
Figure 5B:
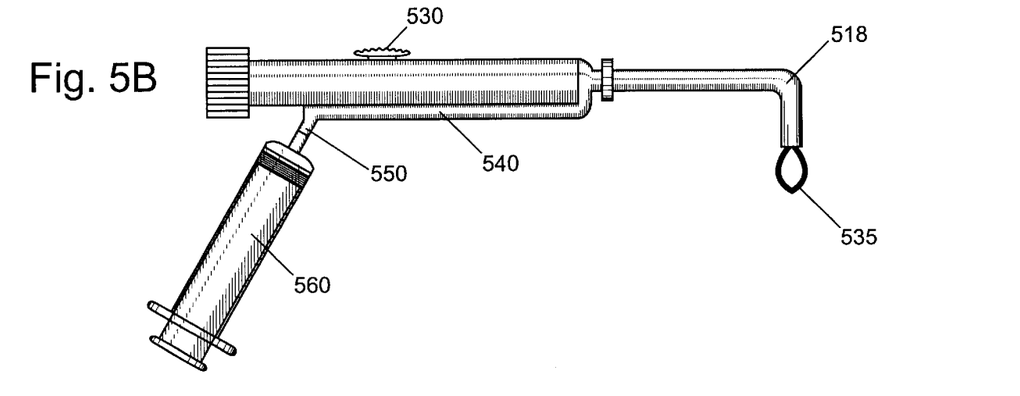
Figure 5C:
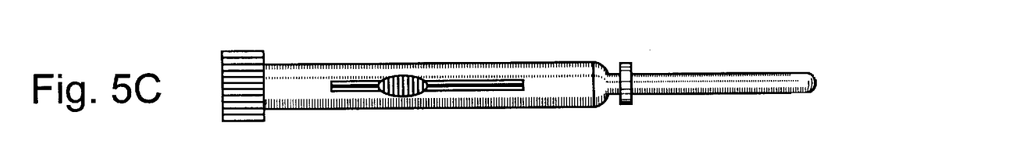

FIG. 5 provides an external, or solid depiction of the device embodied in FIG. 3. In FIG. 5A, a side view of device 500 is portrayed with filament 535 retracted within housing aperture 520 prior to insertion into the bone cavity, and having optional power shaft coupler 532 positioned at the distal end of the device. In FIG. 5B, slide 530 is moved along housing 510 (toward the proximal end) and filament 535 protrudes from aperture 520. In addition, the device depicted in FIG. 5B includes syringe 560 attached to second opening 550 of aspiration tube 540. FIG. 5C provides a top, or birds-eye view of device 500 with L-bend 518 directed away from view.

Figure 6A:
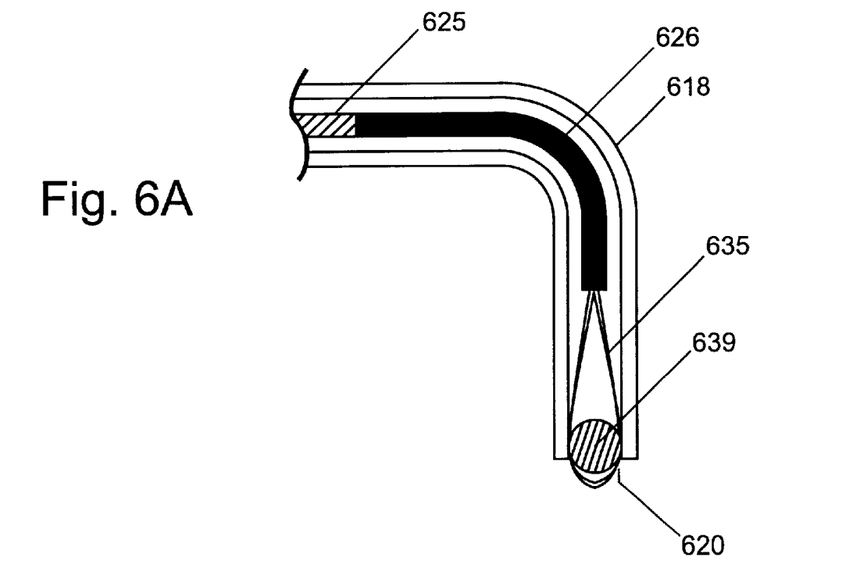
Figure 6B:
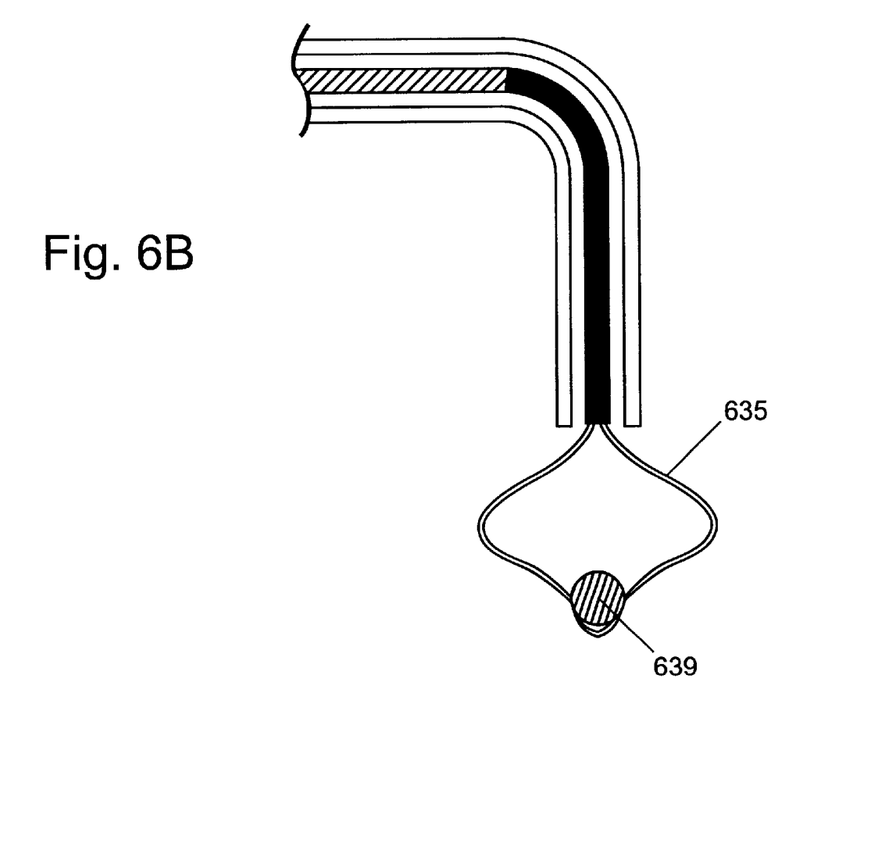

FIG. 6 is a close-up illustration of another filament embodiment of the present invention. Depicted is first housing end 611 including exemplary filament 635 and optional L-bend 618 of the devices of the present invention. FIG. 6A depicts the flexible proximal end 626 of plunger body 625 and attached cutting ribbon (e.g., filament) 635, both of which are retracted into housing aperture 620. FIG. 6B shows how cutting ribbon 635 expands upon ejection from housing aperture 620. Expansion of cutting ribbon 635 is facilitated by optional bauble 639. In some embodiments, optional bauble 639 also provides a mechanism for partially or fully sealing aperture 620 when the filament (i.e., cutting ribbon 635) is retracted into the housing.

Figure 7:
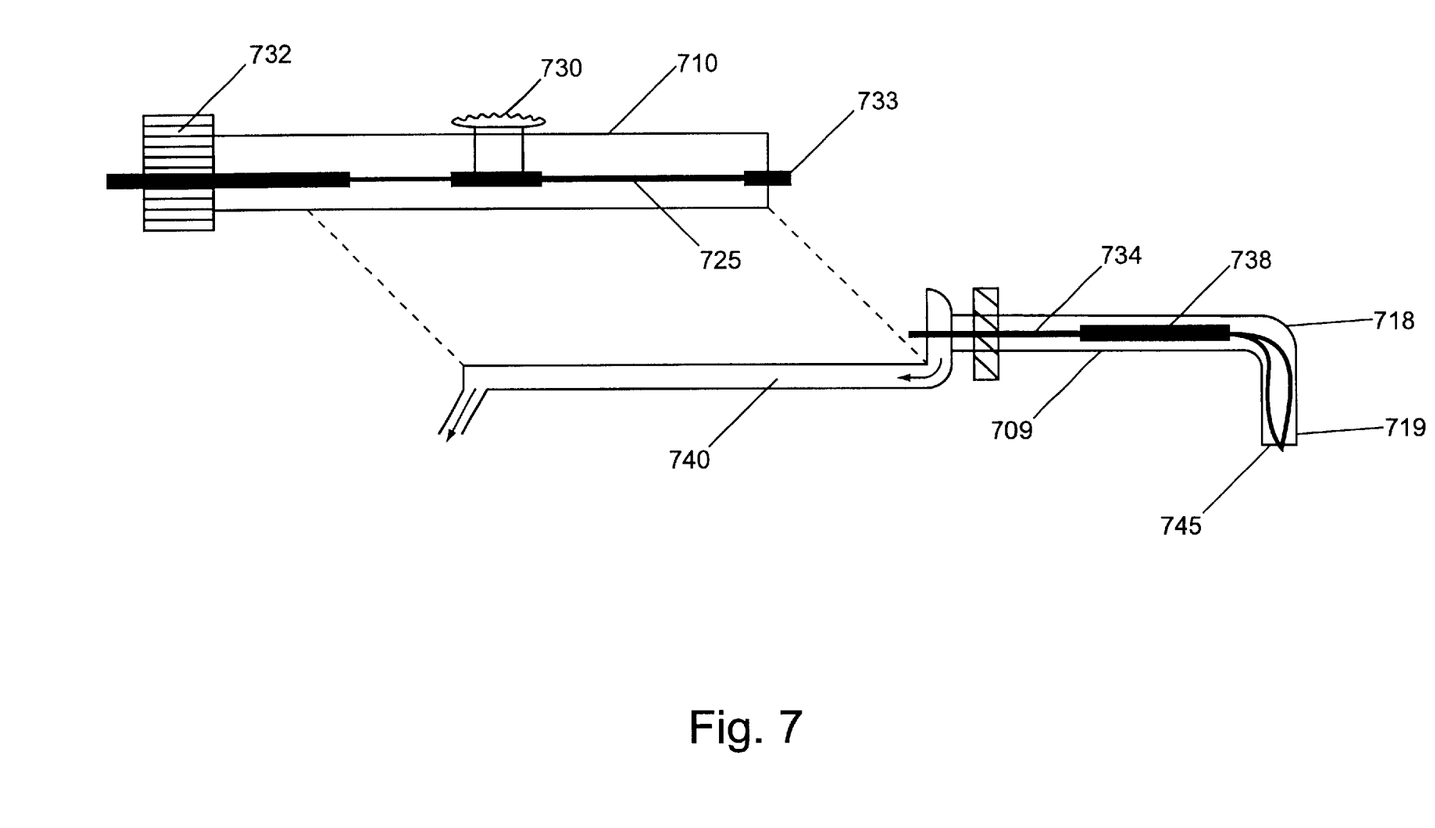
FIG. 7 depicts an additional embodiment of the devices of the present invention having a disposable component.

FIG. 7 further describes a two-piece embodiment of the present invention having disposability aspects. In this embodiment, the housing comprises two pieces: harvesting housing 709 having (in this embodiment) optional L-bend 718 proximal to the insertion tip 719, as well as aspiration tube 740; and plunger housing 710 containing plunger body 725 and slide 730, as well as optional power shaft coupler 732. Optionally, filament 735 is incorporated into harvesting housing 709, whereby both of which can be disposed after exposure to cellular material, leaving an uncontaminated (e.g., non-exposed) plunger housing 710 for use in additional procedures.

Filament 735 is coupled to plunger extension 734 having at least one optional flexible region 738 proximal to filament 735. Optional flexible region 738 allows plunger extension 734 to move past optional L-bend 718 during expulsion of filament 735 into the cavity. Plunger extension 734 and plunger body 725 are removably coupled via plunger linker 733. Plunger housing 710 mates with harvesting housing 709, such that plunger linker 733 connects plunger body 725 and plunger extension 734, thereby translating any movement from slide 730 and concomitant shift in position of plunger body 725 to plunger extension 734 and attached filament 735. Material aspirated from the bone cavity (via a syringe, vacuum jar, or other means of providing a vacuum) travels along the lumen of harvest housing 709 to aspiration tube 740, and on to an optional storage receptacle (e.g., the housing lumen functions as an extension of aspiration tube 740). In an alternate embodiment of the present invention, an additional housing lumen (separate from that containing the filament) is provided as part of the harvesting housing, providing a conduit to the aspiration tube.

Typically, a collection device is provided for coupling to (or preassembled with) the disposable harvest housing. In one preferred embodiment, the collection device is a collection bag. In another embodiment, the collection device is a vacuum jar, thereby providing both the mechanism for generating a vacuum and the collection means in a single element. Alternatively, the aspirated material can be stored temporarily in aspiration tube 740.

Figure 8:
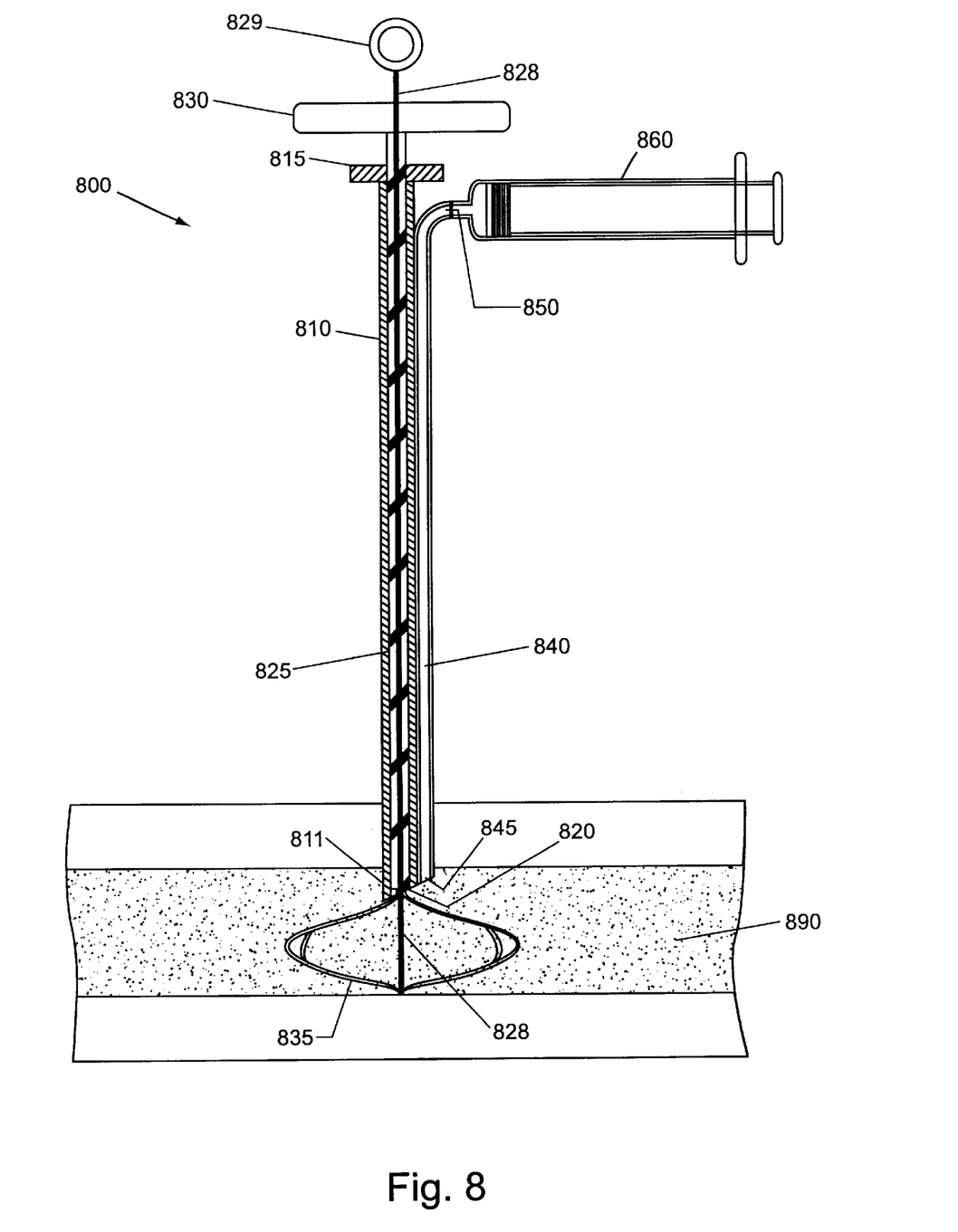
FIG. 8 provides another embodiment of the devices of the present invention having a stabilizing wire associated with the plunger/filament assembly.

FIG. 8 provides yet another embodiment of the present invention. In this embodiment, device 800 includes housing 810 having first housing end 811 (at the proximal end of the device) and second housing end 812 (at the distal end of the device). Housing 810 encompasses a lumen having first lumen aperture 820 and second lumen aperture 822, and containing plunger body 825. Plunger body 825 runs the length of housing 810 and extends beyond optional stop 815 to plunger handle 830 at the distal end, and is coupled to filament 835 at the proximal end.

Plunger body 825 and plunger handle 830 further include adjoining lumens having center shaft/filament stabilizer 828 positioned therein. Center shaft/filament stabilizer 828 is coupled at a proximal end to a portion of filament 835, and at a distal end to stabilizer handle 829. During use, center shaft/filament stabilizer 828 and filament 835 are extended together (via movement of both stabilizer handle 829 and plunger handle 830, thereby adding rigidity and stability to filament 835. Once center shaft/filament stabilizer 828 is extended to a desired length (e.g., positioned with the proximal end adjacent to the far wall of the cavity), filament 835 can be further extended laterally (e.g. sideways, or along the z-axis as compared to the x-y line of center shaft/filament stabilizer 828) into the bone cavity. Furthermore, center shaft/filament stabilizer 828 can also optionally function as a stylus in prevent occlusion of the housing lumen during the bone penetration.

In another embodiment (not shown), the devices of the present invention includes a housing having a single lumen that can carry out the functions of both the housing lumen (e.g., element 105 in FIG. 1) and the aspiration tube (corresponding element 140). In this aspect of the invention, the device includes an optional cutting tool at the first or proximal end of the device to facilitate entry of the housing/aspiration lumen aperture into the bone cavity. Optionally, a solid stylus can be placed into the combination lumen to prevent occlusion of the lumen during the bone penetration and removed during subsequent operations. After penetration, the stylus is removed, and a plunger with attached filament is passed through the lumen so that the filament extends into the marrow cavity. Preferably, the plunger body is thinner in diameter than the internal diameter of the housing/aspiration lumen, e.g., to allow passage of released fluids or materials. A resilient seal, such as, e.g., a rubber or silicone O-ring, can be used to seal the plunger body with the housing lumen. An aspiration port is positioned in fluid contact with the housing/aspiration lumen to allow a vacuum to be applied to the lumen. With such a device, marrow cells are aspirated through the housing lumen and past the plunger body, while the filament is being rotated to disrupt bone cavity material to release marrow cells.

Methods of Extraction

The present invention also provides methods for extracting contents from a bone cavity. The methods include the steps of a) inserting a proximal end of an extraction device into the bone cavity; b) extending a filament from the device into the bone cavity; c) rotating the filament thereby disrupting a localized cellular matrix; and d) aspirating components of the disrupted matrix, thereby extracting contents from the bone cavity.

The bone cavity penetrated during the methods of the present invention can include, but are not limited to, cavities of the iliac crest, the jaw bone, the sternum, the tibia, and the like. Anesthesia and appropriate skin preparation at the selected site are typically performed according to methods known to one of skill in the art. Insertion of the proximal end of the extraction device is performed by placing the proximal end of the device against a bone surface (e.g., a cortical bone margin), and pressing the device against the bone surface until the proximal end has entered the bone cavity. Optionally, the epidermal layer of the skin can be pierced by a scalpel prior to employment of the device. Preferably, the proximal end of the device includes a piercing mechanism, thereby facilitating entry to the bone cavity.

If necessary after traversal of the epidermal layer and subcutaneous tissue, the device is redirected to the specific desired angle of entry into the bone cavity. The desired angle of entry will be dependent in part upon the site selected as well as any anatomical landmarks of the particular patient. In one embodiment of the methods of the present invention, linear force is applied to the device, typically to the distal end. The force must be sufficient to push the proximal end of the device through the wall of the bone cavity (e.g. the proximal cortical bone layer) without damaging the far wall (the distal cortical bone layer) or exiting the cavity. Where the piercing mechanism is, e.g., a sharp angular or circular tip, penetration of the bone cortex requires a linear vector of force along the axis of the housing lumen of up to, for example, about 70 $kg/cm^2$. In another embodiment, the proximal end of the device includes a piercing mechanism with a screwing or drilling mechanism requiring considerably less linear force but input of rotational force to progressively break up or remove overlying cortical bone. Such rotational force can be provided by, e.g., a hand-operated or electric motor powered mechanism. A stop mechanism, such as an adjustable locking collar about the housing, can be employed to prevent excessive penetration as the piercing mechanism enters the marrow cavity.

In some embodiments of the methods of the present invention, the extraction device has an L-bend at the proximal end. When using this class of extraction device, insertion of the proximal end of the device further includes the optional step of rotating the proximal end of the device such that the L-bend is maneuvered within the bone cavity. Preferably, the rotation and concomitant insertion of the proximal end of the device is performed prior to extending the filament.

As noted in the above descriptions of devices appropriate for use in the methods of the present invention, the filament of the extraction device is coupled to a plunger body having a plunger handle. While the plunger handle can assist in the insertion of the device; it is primarily used to extend and retract the filament into the bone cavity. The step of extending the filament typically involves moving the plunger handle toward the proximal end of the housing, thereby moving the plunger body along the housing lumen and concomitantly shifting the filament out of the first lumen aperture and into the bone cavity. The filament is advanced into the marrow cavity an appropriate distance (e.g., about 5 mm to about 25 mm) as determined by the style of filament used and the bone cavity involved. Optionally, a portion of the plunger body is fitted with screw threads that mate to threads on the inner diameter of the housing lumen. In these embodiments, turning or rotating the plunger handle leads to a meterable movement of the plunger body and extension of the filament into the bone cavity.

In embodiments in which the plunger handle is an ergonomically fitted grip or a knob, the handle is typically grasped during movement. In embodiments in which the handle is a slide or button, the plunger handle may only need to be pressed into position, e.g., by thumb pressure, in order to deploy the filament.

Prior to (and/or concomitant with) aspiration of the bone cavity contents, the filament is moved or rotated within the bone cavity. Movement of the filament disrupts any localized cellular matrix, such as the trabecula or connective tissue. Translocation of the filament can be achieved manually (e.g., by turning, rotating, or otherwise manipulating the plunger body via the handle), or the plunger body and/or handle can be coupled to an external power source, such as the power shaft of a dental handpiece (see, for example, U.S. Pat. No. 6,425,761 to Eibofner "Drive system for dental handpiece"; U.S. Pat. No. 6,273,718 by Schwenoha, "Dental handpiece"; U.S. Pat. No. 6,270,345 to Abbott "Vane motor for dental and medical handpieces" and references cited therein) or other commercially-available devices from, e.g., Abbott Laboratories (Abbott Park, Ill.) American Dental Technologies (Corpus Christi, Tex.), Baxter Scientific Products (Deerfield, Ill.), Sybron Dental Specialties (Orange, Calif.), and the like.

The degree of rotation of the filament within the bone cavity can range from a small degree (e.g., about 5°, 10° 15°) for a small or tight enclosure, to 180° or 360° for a fairly expansive compartment. In some embodiments of the invention, the filament can be repeatedly rotated about a full circle. Intermediate angles of rotation (for example, a 45°, 90°, 120° or 270° rotation) are also contemplated in the methods of the present invention. The optimal degree of rotation and number of rotation movements will depend upon the size of the bone cavity, type of filament employed, and desired extraction volume, and as such can be easily determined by one of skill in the art without excess experimentation.

Optionally, the methods of the invention includes embedding or otherwise pivotably-engaging an end of the filament and/or a stabilizing wire at an opposing marrow cavity wall to enhance the efficiency and/or accuracy of disruption of the matrix during use. For example, one embodiment of the filament includes an embedding point, which can be removeably implanted into a far wall of the bone cavity. The body of the filament is then gyrated between the two fixed points (e.g., the aperture of the device and the opposite wall of the cavity). Filament greater in length than the distance across the marrow cavity can be extended into the cavity, e.g., so that undulations of excess filament can extend into cavity recesses during rotational movements thereby disrupting hard to reach bone marrow cells.

Aspiration of the released cavity contents is typically accomplished by applying a vacuum or partial vacuum (i.e., less than atmospheric pressure) to the device via the aspiration tube. In one embodiment of the methods, aspiration is performed by attaching a syringe to a second opening of the aspiration tube and partially withdrawing the syringe plunger. In another embodiment, a container having a partial vacuum in place (e.g., a vacuum jar) is attached to the aspiration tube. Optionally, the extraction device is equipped with such a collection device. Alternatively, a collection receptacle coupled to a vacuum pump is attached to the aspiration tube, thereby providing a mechanism for collecting aspirated cavity contents. The volume of material aspirated can vary widely depending, e.g., on factors such as the condition of the patient, the location of the extraction, the forces employed, the ratio of marrow to blood retrieved, and the like. Typically, between about 0.5 mL and about 10 mL of marrow material is extracted during a single penetration; however, blood volume will increase the total volume aspirated during the procedure. For example, the volume (including blood) extracted from a single insertion at the iliac crest of a small child can be about 2 to about 10 milliliters, whereas a similar extraction from a healthy adult male can provide about 200 to about 300 milliliters, or more of aspirate. It is an aspect of the invention that the number of stem cells obtained per milliliter of aspirate can be higher than for the prior art due to the enhanced release of bone marrow cells during aspiration, thus requiring lower aspirate volumes overall.

Optionally, rotation of the filament and aspiration of the released cavity contents is performed in a concomitant manner (either simultaneously, or by repeatedly alternating between rotation of the filament and aspiration of released contents in rapid succession). In some embodiments of the methods of the present invention, rotation of the filament is preceded by extension of a thin sleeve or housing proximal to the first lumen aperture of the device (i.e., where the filament extends from the housing), which facilitates a more complete and/or free rotation of the filament within the cavity during disruption of the marrow tissue.

Optionally, the procedure can be repeated at a secondary bone cavity entry site, until an adequate extraction volume or cell count is generated. Once the extraction process has been competed, the filament is withdrawn into the device (by movement of the plunger handle) and the device is removed from the bone cavity. At this point, standard post-operational procedures are exercised, such as application of an appropriate pressure dressing, and bandaging of the incision.

Additional Embodiments

Devices and methods of the invention can be modified, e.g., to allow pathologists to obtain clinical samples for analysis, to provide biopsy samples (when larger volume or multiple samples are desired), and the like. As analytical methods generally require less sample that therapeutic regimes such as bone marrow transplants, the devices can be smaller in scale. Such devices can provide adequate clinical samples form smaller bones than standard techniques.

The present invention also provides devices and methods for delivery of a composition, such as a drug, cell, chemical, or combination thereof. For example, a preparation of stem cells or a chemotherapy for treatment of, e.g., a leukemia or bone cancer, can be directly administered to a bone cavity using the devices of the present invention. The housing lumen and/or the aspiration tube can be used to administer a composition to the bone cavity after penetration of the cavity by the device. For example, pharmaceutical compositions can be administered within a bone marrow cavity by filling the aspiration tube and/or collection receptacle with the composition and pressurizing the aspiration system to force the composition into the cavity. In another example, a luer-lock port can be installed in fluid contact with the aspiration tube or housing lumen to allow direct injection of pharmaceutical compositions into the bone marrow cavity using a standard syringe.

Furthermore, the present invention provides devices and methods for deployment of one or more diagnostic devices inside a cavity, such as a bone cavity. For example, drug releasing/dispensing devices, cell growth hormone sources, radiation sources, and stem cell "farms" or other cell culturing devices are just a few potential devices that could be deployed in the bone cavity using the device and/or methods of the present invention.

Modifications can be made to the methods and devices as described above without departing from the spirit or scope of the invention as claimed, and the invention can be put to a number of different uses, including:

The use of any method herein, to extract material from a bone cavity.

The use of any device or integrated system as described herein, to extract material from a bone cavity.

An assay, kit or system utilizing a device of the present invention, or use of any one of the extraction strategies or methods hereinbefore described. Kits will optionally additionally include one or more of: instructions for operating the devices of the present invention, instructions for performing the methods of the present invention, one or more containers which contain sterile solutions, device or system components, marking devices, packaging materials, or the like.

In a further aspect, the present invention provides for the use of any provided device herein for the practice of any method herein.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A device for extracting material from a bone cavity, the device comprising:
a housing comprising a lumen running a length of the housing, a first lumen aperture at a first end of the housing, and a second lumen aperture at a second region of the housing;
a plunger body, wherein the plunger body is slideably positioned within and extends at least a part of the length of the lumen;
one or more filaments coupled to a first end of the plunger and positioned proximal to the first end of the housing;
a handle coupled to a second end of the plunger, wherein the handle extends beyond the second region of the housing; and
an aspiration tube cojoined to a portion of the housing, wherein the aspiration tube comprises a first aspiration aperture proximal to the first lumen aperture.

2. The device of claim 1, wherein the housing further comprises a piercing mechanism at the first end of the housing proximal to the first lumen aperture.

3. The device of claim 1, wherein the first lumen aperture and the first aspiration aperture are adjacently positioned to provide a piercing mechanism for insertion of the apertures into the bone cavity.

4. The device of claim 1, wherein the housing further comprises a stop at the second region of the housing.

5. The device of claim 1, wherein the plunger comprises a screw-threaded plunger portion and the lumen comprises inner screw threads for metering insertion of the filament into the bone cavity.

6. The device of claim 1, wherein the one or more filaments further comprises a stabilizing wire.

7. The device of claim 6, wherein the stabilizing wire further comprises a pointed region.

8. The device of claim 1, wherein a member of the one or more filaments comprises a rigid piece of plastic or metal having one or more looped extensions.

9. The device of claim 8, wherein the metal comprises stainless steel, surgical stainless steel, or titanium.

10. The device of claim 8, wherein the rigid piece comprises a shape memory wire.

11. The device of claim 8, wherein the filament member comprises a cutting edge.

12. The device of claim 1, wherein the filament member comprises one or more brush-like members.

13. The device of claim 1, wherein the handle comprises an ergonomically-shaped member.

14. The device of claim 1, wherein the handle comprises a knob.

15. The device of claim 1, wherein the aspiration tube further comprises a vacuum mechanism positioned at a second aspiration aperture.

16. The device of claim 15, wherein the vacuum mechanism comprises a syringe.

17. The device of claim 15, wherein the vacuum mechanism comprises a vacuum pump.

18. The device of claim 15, further comprising a collection device coupled to the vacuum mechanism of the aspiration tube.

19. The device of claim 1, wherein the housing comprises a multi-lumen structure encompassing both the lumen and the aspiration tube.

20. The device of claim 1, further comprising a sleeve encompassing the housing and the aspiration tube.

21. A device for extracting material from a bone cavity, the device comprising:
a housing comprising a lumen running a length of the housing, a first lumen aperture at a first end of the housing, and a second lumen aperture at a second region of the housing;
a plunger body, wherein the plunger body is slideably positioned within and extends at least a part of the length of the lumen;
one or more filaments coupled to a first end of the plunger and proximal to the first end of the housing;
a handle coupled to a second end of the plunger, wherein the handle extends beyond the second region of the housing; and
an aspiration port in fluid contact with the lumen, by which bone cavity material disrupted by the one or more filaments can be extracted.

22. A method for extracting contents from a bone cavity, the method comprising:
inserting a proximal end of an extraction device into the bone cavity;
extending a filament from the device into the bone cavity;
rotating the filament and disrupting a localized cellular matrix; and
aspirating components of the disrupted matrix, thereby extracting contents from the bone cavity.

23. The method of claim 22, wherein inserting the proximal end of the extraction device comprises:
placing the proximal end of the device against a bone surface, wherein the proximal end of the device comprises a cutting mechanism; and
pressing the cutting mechanism against the bone surface and entering the bone cavity.

24. The method of claim 23, further comprising:
rotating the proximal end of the device within the bone cavity prior to extending the filament.

25. The method of claim 22, wherein extending the filament comprises:
grasping the plunger handle and moving the handle toward the proximal end of the housing, thereby moving a plunger body along a lumen and propelling the filament out of a first lumen aperture and into the bone cavity.

26. The method of claim 22, wherein extending the filament comprises:
rotating the plunger handle, thereby moving the a screw-threaded plunger body along a screw threaded lumen and shifting the filament out of the first lumen aperture and into the bone cavity.

27. The method of claim 22, wherein rotating the filament comprises turning the plunger handle.

28. The method of claim 22, wherein rotating the filament comprises coupling the plunger body to a power shaft of a dental handpiece.

29. The method of claim 22, wherein aspirating the released cavity contents comprises coupling a vacuum mechanism to the device.

30. The method of claim 22, wherein extending and rotating the filament are performed concomitantly.

31. The method of claim 22, wherein rotating the filament and aspirating the released cavity contents are performed concomitantly.

32. The method of claim 22, wherein the bone cavity comprises a cavity in a bone selected from the group consisting of an iliac crest, a jaw bone, a sternum, and a tibia.

* * * * *